United States Patent [19]

Otani et al.

[11] 4,321,376
[45] Mar. 23, 1982

[54] NEPLANOCIN-B AND -F

[75] Inventors: Masaru Otani; Satoshi Yaginuma; Masatoshi Tsujino; Naoki Muto; Tetsu Saito, all of Shizuoka; Tadashiro Fujii, Mishima, all of Japan

[73] Assignee: Toyo Jozo Kabushiki Kaisha, Shizuoka, Japan

[21] Appl. No.: 101,126

[22] Filed: Dec. 7, 1979

[30] Foreign Application Priority Data

Feb. 23, 1979 [JP] Japan .................................. 54-21201

[51] Int. Cl.³ ............................................ C07D 473/32
[52] U.S. Cl. .................................... 544/277; 424/253; 435/122
[58] Field of Search ......................... 544/277; 424/253

[56] References Cited

U.S. PATENT DOCUMENTS 4,138,562  2/1979  Vince .................................. 544/277

*Primary Examiner*—Nicholas S. Rizzo
*Attorney, Agent, or Firm*—Young & Thompson

[57] ABSTRACT

Neplanocin-B and -F of the formula

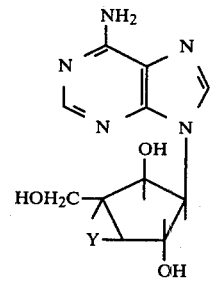

in which Y is oxygen or a valence bond, are produced by culturing Ampullariella sp. A 11079 FERM-P No. 4494 in a nutrient medium and then separating the neplanocin-B and -F thus produced from the culture medium.

3 Claims, 6 Drawing Figures

NEPLANOCIN-B AND -F

The present invention is concerned with the novel substances neplanocin-B and -F, and with a process for the preparation thereof.

The preparation thereof comprises culturing a neplanocin-producing microorganism Ampullariella sp. A 11079 FERM-P No. 4494 in a nutrient medium and isolating the novel substances neplanocin-B and -F therefrom.

This application is related to our copending application Ser. No. 18,790, filed Mar. 8, 1979, now abandoned.

Thus, according to the present invention, there are provided the novel substances neplanocin-B and -F of the formula

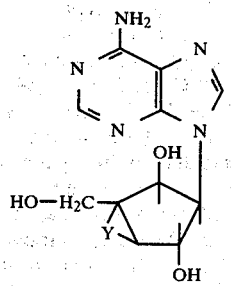

wherein Y is oxygen or a valence bond.

Neplanocin B, in which Y is oxygen, has the following physico-chemical properties:

(1) Elementary analysis: C 47.44%; H 4.63%; N 25.07%

(2) Molecular weight: (calculated from the mass spectrum analysis) 279

(3) Molecular formula: $C_{11}H_{13}N_5O_4$ (4) Melting point: 269°–272° C. (decomp.)

(5) Specific rotation: $[\alpha]_D^{24} = -3.5$ (c=1.0% in dimethyl sulphoxide)

(6) Ultra-violet absorption spectrum:
in $H_2O$: shown in FIG. 1 of the accompanying drawings
$\lambda max = 262$ m$\mu$, $E_{1\ cm}^{1\%} = 530.4$
in acidic water: (one drop of 0.1 N HCl)
$\lambda max = 259$ m$\mu$, $E_{1\ cm}^{1\%} = 506.7$
in alkaline water: (one drop of 0.1 N NaOH)
$\lambda max = 263$ m$\mu$, $E_{1\ cm}^{1\%} = 522.2$ (7) Infra-red absorption spectrum (KBr): shown in FIG. 2 of the accompanying drawings.
Absorption bands at 3380, 3280, 3100, 2920, 2880, 2740, 1700, 1610, 1570, 1520, 1480, 1420, 1380, 1350, 1300, 1250, 1220, 1170, 1160, 1100, 1080, 1030, 1020, 980, 970, 870, 840, 790, 730 and 710 cm$^{-1}$.

(8) NMR spectrum: shown in FIG. 3 of the accompanying drawings. (internal standard DSS, in deuterium dimethyl sulphoxide, 100 MHz).

(9) Solubility:
Soluble: water and dimethyl sulphoxide.
Insoluble: ethyl acetate, chloroform, benzene and diethyl ether.

(10) Color reaction:
Slightly positive: decolorization of potassium permanganate.
Negative: ninhydrin, Molisch's reagent and anisaldehyde.

(11) Nature: weakly basic.

(12) Color: white crystalline platelets.

(13) Rf value (silica gel f, Tokyo Kasei Co.):
n-butanol:acetic acid:water (6:1:1 v/v/v); Rf=0.42
n-butanol:conc. aq. ammonia:water (10:0.5:2 v/v/v); Rf=0.27
n-propanol:conc. aq. ammonia:water (10:1:1 v/v/v); Rf=0.41
acetone:water (10:1 v/v); Rf=0.48

(14) Chemical structure:

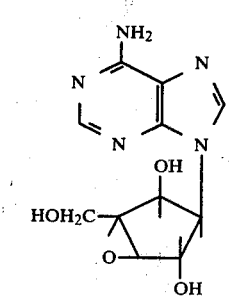

Neplanocin F has the following physico-chemical properties:

(1) Elementary analysis: C 48.74%; H 4.83%; N 25.71% (contains water of crystallization)

(2) Molecular weight (calculated from the mass spectrum analysis): 263

(3) Molecular formula: $C_{11}H_{13}N_5O_3 \cdot \frac{1}{2}H_2O$ (4) Melting point: 223° C. (decomp.)

(5) Specific rotation: $[\alpha]_D^{21} = -6.6$ (c=0.8% in water)

(6) Ultra-violet absorption spectrum:
in $H_2O$: shown in FIG. 4 of the accompanying drawings
$\lambda max = 263$ m$\mu$, $E_{1\ cm}^{1\%} = 548.7$
in acidic water (one drop of 0.1 N HCl):
$\lambda max = 260$ m$\mu$, $E_{1\ cm}^{1\%} = 527.1$
in alkaline water (one drop of 0.1 N NaOH):
$\lambda max = 263$ m$\mu$, $E_{1\ cm}^{1\%} = 531.8$ (7) Infra-red absorption spectrum (KBr): shown in FIG. 5 of the accompanying drawings.
Absorption bands at 3320, 3210, 2920, 1650, 1610, 1580, 1480, 1420, 1380, 1340, 1310, 1270, 1220, 1180, 1110, 1070, 1020, 980, 900, 840, 800 and 730 cm$^{-1}$.

(8) NMR spectrum: shown in FIG. 6 of the accompanying drawings (internal standard DSS, in deuterium dimethyl sulphoxide, 100 MHz).

(9) Solubility:
Soluble: water, dimethyl sulphoxide and acetic acid.
Insoluble: ethyl acetate, chloroform, benzene and diethyl ether.

(10) Color reaction:
Positive: decolorization of potassium permanganate.
Negative: ferric chloride, ninhydrin and Fehling's reagent.

(11) Nature: weakly basic.

(12) Color: white crystalline needles.

(13) Rf value (silica gel f, Tokyo Kasei Co.):
n-butanol:acetic acid:water (6:1:1 v/v/v); Rf=0.51
n-butanol:conc. aq. ammonia:water (10:0.5:2 v/v/v); Rf=0.43
n-propanol:conc. aq. ammonia:water (10:1:1 v/v/v); Rf=0.59
acetone:water (10:1 v/v); Rf=0.48.

(14) Chemical structure:

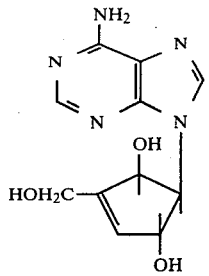

The biological properties of neplanocin B and F are as follows:

(1) Acute toxicity:

No mortalities were observed when 100 mg/kg of neplanocin B or F were administered intraperitoneally to mice.

(2) Cell growth inhibitory activity:

The growth of mouse lymphoma cell L 5178Y culture was inhibited at a concentration of 0.8 γ/ml neplanocin B and 20 γ/ml neplanocin F, respectively.

(3) Other activity:

1. Neplanocin B also has an anti-depressant activity.

2. To platelet-rich plasma of rabbit (to rabbit blood 9 parts was added 3.8% sodium citrate aqueous solution one part, and centrifuged at room temperature for 15 minutes at 900 r.p.m.) (0.9 ml) was added neplanocin-F saline solution ($3 \times 10^{-4}$ g/ml, 0.05 ml) and the mixture was incubated at 37° C. After three minutes adenosine diphosphate solution (0.05 ml) was added up to a final concentration of $10^{-6}$ M and the percent of aggregation was assayed. The inhibition percent of aggregation of neplanocin-F was 52.2±8.27% (means value±standard deviation: N=5) which shows utility as an anti-thrombosis agent.

The neplanocin-producing microorganism was isolated from a soil sample collected in an onion field at Niigata-ken, Japan and belongs to genus Ampullariella. The strain is referred to as Ampullariella sp. A 11079 and has been deposited in the permanent collection at The Institute for Microbial Industry and Technology, Japan, under the designation FERM-P No. 4494.

Ampullariella sp. A 11079 FERM-P No. 4494 has the following taxonomic characteristics:

(I) Morphological characteristics:

Observations on an inorganic salts-starch agar medium at 30° C. for 10–15 days culture were as follows:

Strain A 11079 produces a curved and branching substrate mycelium, 0.5–0.8μ in diameter and a slightly immature aerial mycelium.

Sporangiophores grown on substrate mycelium have sporangia and the sporangium has a cylindrical or bottle shape measuring from $5-15 \times 10-25\mu$. Many sporangiospores are arranged in parallel chains within the sporangium. The sporangiopores have tufts of polar flagella, are motile in water and are rod shaped, measuring from $0.5-1.0 \times 1.0-2.0\mu$.

(II) Composition of diaminopimelic acid:

Diaminopimelic acid detected by whole cell analysis is of the meso- and hydroxy-type.

(III) Cultural characteristics on various media:

The observation results of cultural characteristics in various media at 30° C. for 20 days culture are shown in the following Table 1. No aerial mycelium was observed except for a slight formation of immature growth aerial mycelia on inorganic salts-starch agar medium and oatmeal agar medium.

The indication of the color is based upon the indication given in "Color Harmony Manual", 4th Ed., 1958, published by Container Corporation of America.

(IV) Physiological properties:

Physiological properties are illustrated as follows:

1. Utility of carbon sources:

| Carbon source | Utilization | Carbon source | Utilization |
|---|---|---|---|
| L-arabinose | + | salicin | + |
| D-xylose | + | D-galactose | + |
| D-glucose | + | glycerol | + |
| D-fructose | + | L-sorbose | − |
| D-mannose | + | trehalose | + |
| D-mannitol | + | α-melibiose | − |
| inositol | − | D-ribose | − |
| L-rhamnose | + | maltose | + |
| sucrose | + | melezitose | − |
| β-lactose | − | D-cellobiose | + |
| raffinose | − | D-sorbitol | − |
| cellulose | − | dulcitol | − |
| starch | + | | |

(+ = positive; − = negative)

TABLE 1

Cultural characteristics on various media

| Medium | Growth | Sporangium | Colour of substrate mycelium | Soluble pigment |
|---|---|---|---|---|
| Sucrose-nitrate agar | poor to medium | few | pearl pink (3 ca) - light melon yellow (3ea) | none |
| Glucose-asparagine agar | medium to poor | few | bamboo (2fb) - pearl pink (3 ca) | none |
| Glycerol-asparagine agar | poor to medium | none | bamboo (2fb) - pearl pink (3ca) | none |
| Inorganic salts-starch agar | good to medium | good | amber (3lc) - pastel orange (4ic) | none |
| Tyrosine agar | poor to medium | none | light amber (3ic) | none |
| Oatmeal agar | good | medium | amber (3lc) - bright maize (3la) | none |
| Yeast-malt agar | good to medium, slight wrinkles | poor | topaz (3ne) - amber (3pe) | pale amber (3pe) |
| Glucose-yeast extract agar (Waksman medium No. 28)* | medium to good | none | cinnamon (3le) | golden brown (3pg-3pi) |
| Glycerol-nitrate agar | medium | none | colourless - bamboo | none |

TABLE 1-continued

Cultural characteristics on various media

| Medium | Growth | Sporangium | Colour of substrate mycelium | Soluble pigment |
|---|---|---|---|---|
| (Waksman medium No. 1)* | | | (2fb) | |
| Glucose-nitrate agar (Waksman medium No. 1)* | poor medium | none | colourless - bamboo (2fb) | none |
| Nutrient agar | poor | none | light amber (3ic) - cinnamon (3le) | golden brown (3pg) |
| Emerson's agar (Waksman medium No. 28)* | good to medium | none | cinnamon (3le) - camel (3ie) | golden brown (3pg-3pi) |
| Bennett's agar (waksman medium No. 30)* | good to medium | none | amber (3pe) - topaz (3ne) | pale golden brown(3pg) |
| Peptone Czapeck's agar | medium to good | few | light amber (3ic) - amber (3lc) | pale golden brown(3pg) |
| Yeast extract Czapeck's agar | medium to good | few | amber (3lc - 3nc) | none |
| Tyrosine agar**** | poor | none | light tan (3gc) - bisque (3ec) | clove brown (3pl) |
| Peptone-yeast iron agar | medium to poor | none | light amber (3ic) | dark spice brown (4pl) |
| Casein agar**** | good | none | camel (3ie) - cinnamon (3le) | clove brown (3pl) |

*Waksman, S. A., "The Actinomycetes" Vol.2, 1961, p. 327–334, pub. Williams & Wilkins Co.
**J. Elisha Mitchell, Sci. Soc., 79, 54/1963.
***J. Virol., 3, 210/1969.
****J. Bacteriol., 69, 147/1955.

2. Growth temperature:
10°–45° C.
3. Action on skim milk:
peptonization and coagulation positive.
4. Melanin production:
Tyrosine agar medium; negative.
Peptone yeast iron agar medium; positive.
5. Starch hydrolysis:
positive.
6. Cellulose hydrolysis:
negative.
7. Casein hydrolysis:
positive.
8. Gelatine liquefaction:
positive.
9. Tyrosine decomposition:
negative.
10. Xanthine decomposition:
negative.
11. Hypoxanthine decomposition:
negative.
12. Hydrogen sulphide formation:
negative.
13. Nitrate reduction:
negative.

According to the above taxanomical data, wherein the strain A 11079 has sporangia bearing sporangiophores grown on branching substrate mycelium, cylindrical or bottle shaped sporangium, sporangiospores arranged in parallel chains within the sporangium, rod-shaped sporangiospores with tufty polar flagellum and meso diaminopimelic acid, this strain belongs to the genus Ampullariella by consulting "Key to the genera of the family Actinoplanaceae" in Bergey's "Manual of Determinative Bacteriology", 8th Ed., 1974, p. 707–708. Therefore, this strain is referred to as Ampullariella sp. A 11079.

The present invention will now be described in more detail, with reference to the accompanying drawings, in which.

Figure 1:
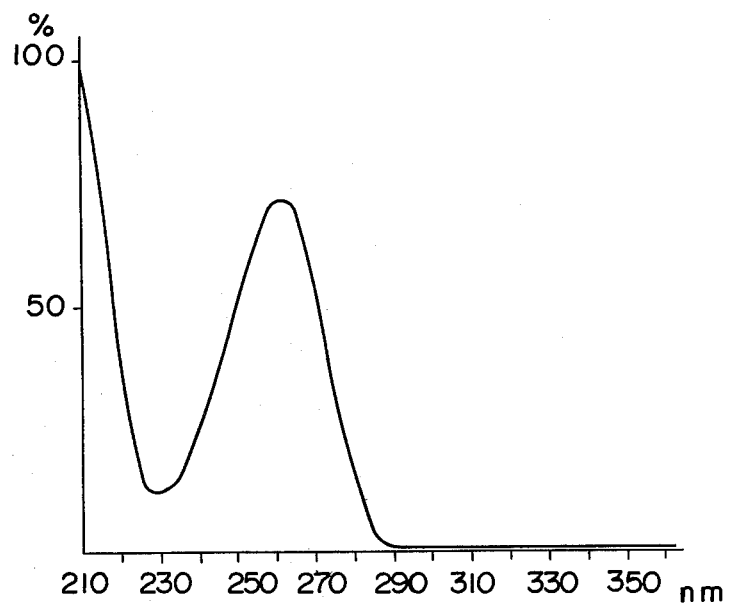
FIG. 1 is the ultra-violet absorption spectrum of neplanocin B.
Figure 2:
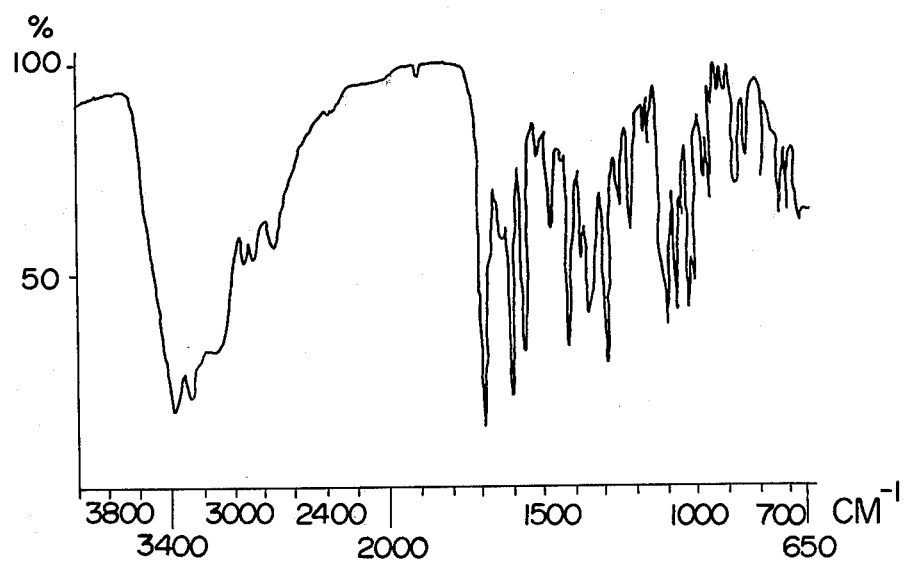
FIG. 2 is the infra-red absorption spectrum of neplanocin B.
Figure 3:
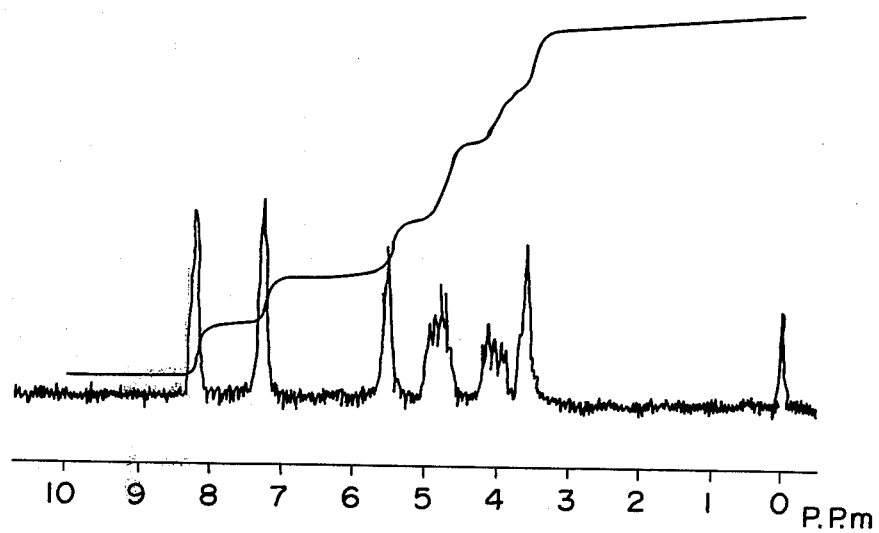
FIG. 3 is the NMR spectrum of neplanocin B.
Figure 4:
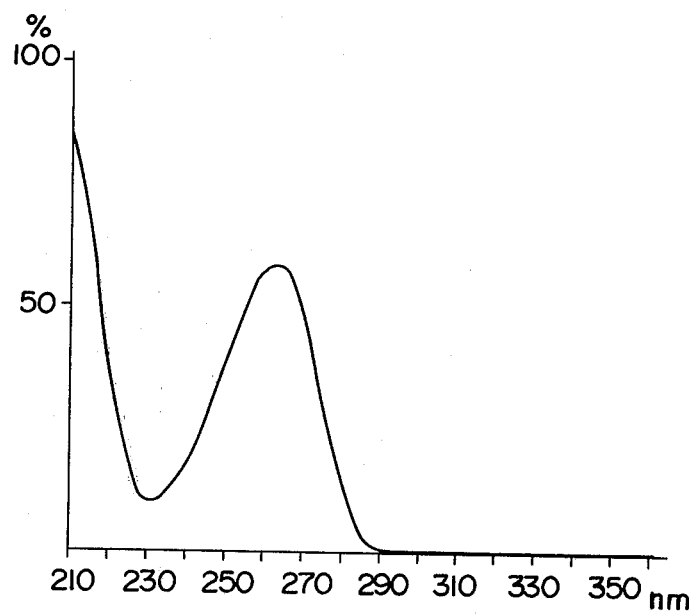
FIG. 4 is the ultra-violet absorption spectrum of neplanocin F.
Figure 5:
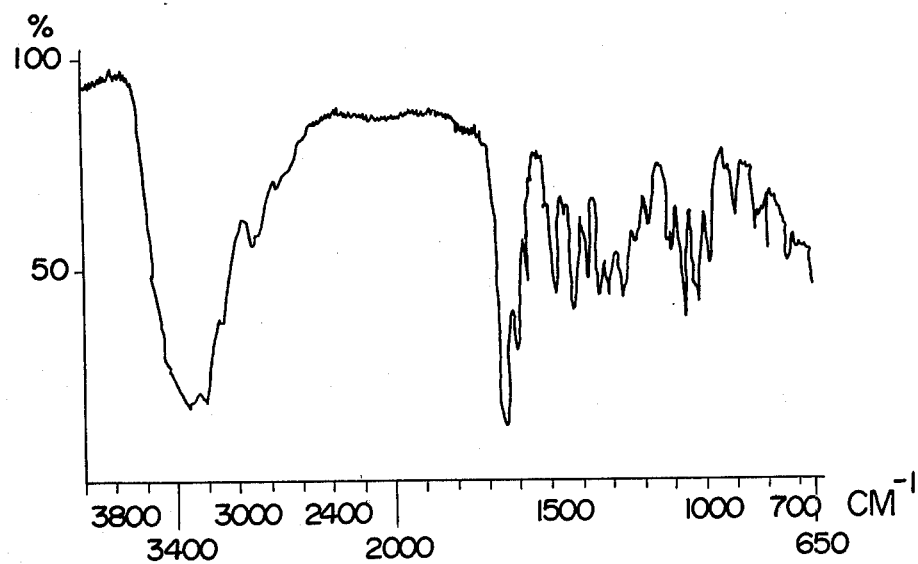
FIG. 5 is the infra-red absorption spectrum of neplanocin F.
Figure 6:
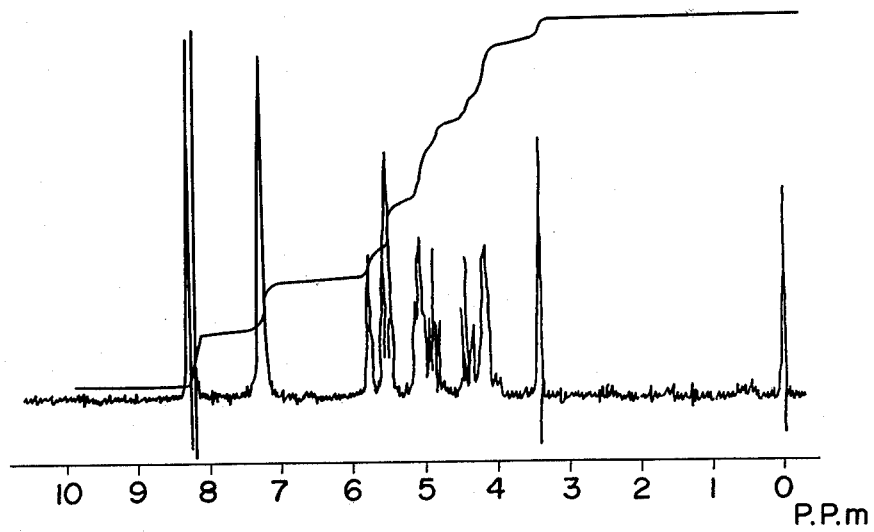
FIG. 6 is the NMR spectrum of neplanocin F.

According to the present invention, the neplanocin-B and -F are produced, for example, by inoculating a strain Ampullariella sp. A 11079 FERM-P No. 4494 into an appropriate nutrient medium. The cultivation of the microorganism can be carried out in a number of different ways, such as in a synthetic or natural medium, using a liquid or solid culture. On an industrial scale, liquid media are preferable. The medium used can contain assimilable carbon and nitrogen sources, inorganic salts and other substances for the antibiotic neplanocin-producing microorganisms. Examples of carbon sources include glucose, sucrose, glycerol, soluble starch, molasses and the like. Assimilable nitrogen sources which can be used include peptone, corn steep liquor, soya bean powder, meat extract, rice bran, casein hydrolysate, nitrate, ammonium salt and the like. Inorganic salts, such as sodium chloride, phosphates (calcium, mangesium, ferrous iron or manganese) can also be used. An anti-foamer, such as a silicone oil or soya bean oil, can also be added.

In the case of liquid culture, a submerged aeration culture is preferred. In this case, the culturing temperature selected is that which is optimum for the microorganisms and is preferably about 25° to 30° C. The cultivation time depends upon the conditions used and is generally from 2 to 4 days. The pH of the medium during culturing is preferably controlled so as to be neutral or slightly acidic. The cultured medium contains the antibiotic neplanocin-B and -F. Isolation of the antibiotic neplanocin-B and -F can be carried out by conventional isolation or separation processes for microorganism metabolites. Since the neplanocin-B and -F are water soluble weakly basic substances, they can be isolated by adsorption on appropriate adsorbents, followed by eluting with an appropriate solvent. Examples of adsorbents which can be used include active carbon, cation exchange resins, active alumina and silica gel. The eluting solvent used depends upon the adsorbent used, for example, a water-miscible organic solvent, such as aqueous methanol, aqueous acetone or aqueous dioxan, or an acidic, alkaline or salt solution.

The neplanocin-B and -F can also be isolated and purified on the basis of the weakly basic nature of these substances. For example, the antibiotics can be adsorbed on a cation exchange resin such as "Amberlite" IRC-50 (registered trademark of Rohm and Haas Co., U.S.A.) or "Dowex" 50 (registered trademark of Dow Chemical Co., U.S.A.), and eluted with an appropriate acidic, alkaline or salt solution.

A combination of adsorbent and ion exchange resin is preferably used for the isolation, elution and purification of the antibiotics. For example, the culture filtrate can be applied to the cation exchange resin "Amberlite" IR-120 to adsorb the antibiotics, then eluted with an alkaline solution, such as 3.7 N aqueous ammonia solution, to give the active fraction and, after adjusting the pH thereof to a neutral or weakly alkaline value, the antibiotics are adsorbed on active carbon, followed by eluting with 70% methanol. The eluant can be adsorbed on the anion exchange resin "Amberlite" IRA-410 and again eluted with water, the active fractions being collected. The combined fractions are concentrated to give a crude material and finally purified by silica gel adsorption chromatography. Further purification can be carried out by recrystallization. The purity as a single substance can be checked by showing a uniform melting point or a single spot on a paper chromatogram, by thin layer chromatography and by paper electrophoresis.

The neplanocin-B and -F of the present invention are useful novel substances, as pointed out above. Also, many biochemically active compounds of nucleic acid-related substances are known; and neplanocin-B and -F not only have the expected pharmacological effect, which is the same as the other purine compounds, but are intermediates for the synthesis of pharmacologically active purines.

The following examples are given for the purpose of illustrating the present invention:

EXAMPLE 1

100 ml. of an aqueous medium (pH 6.5) containing, by weight, 2% glucose, 2% starch, 1% yeast extract, 1% casein hydrolysate and 0.2% calcium carbonate were introduced into a 500 ml. flask and sterilized at 120° C. for 15 minutes. One loopful of slant culture of Ampullariella sp. A 11079 FERM-P No. 4494 was inoculated into two flasks of this medium and shake-cultured at 30° C. After four days, the cultured medium was transferred to 20 liters of the above-described sterilized medium in a 30-liter jar fermenter and cultured at 30° C., with agitation at 300 r.p.m. and aeration at a rate of 20 liters/min., for 48 hours.

The cultured medium was then transferred to 200 liters of an aqueous medium (pH 6.5) containing, by weight, 4% glucose, 1% soya bean powder, 0.4% meat extract, 0.4% peptone, 0.1% yeast extract, 0.25% sodium chloride and 0.1% calcium carbonate and cultured at 30° C., with agitation at 180 r.p.m. and aeration at a rate of 130 liters/min., for 40 hours. The cultured broth obtained (about 200 liters) was filtered and the mycelia washed with water. The filtrate and wash water were combined to give about 140 liters of clear filtrate (potency about 50 mcg/ml).

The filtrate was passed through a column of 20 liters of cation exchange resin "Amberlite" IR-120 (H+ type) to adsorb the material and the column washed with about 100 liters of water. Elution was carried out with 3.7 N aqueous ammonia solution, the primary eluate (30 liters) being discarded. 90 liters of the following eluate were collected, adjusted to pH 8 by adding 6 N hydrochloric acid and then applied to a column of 4 liters of active carbon, washed with water and thereafter eluted with 90 liters of 70% aqueous methanol. The eluate thus obtained was concentrated to give 500 ml. of a concentrate which was left to stand at a low temperature. The precipitate obtained was collected and dried to give crude neplanocin B (5.1 g., purity about 60%, yield 44%).

EXAMPLE 2

The neplanocin B obtained in Example 1 (5.1 g.) was applied to a column of silica gel (8.3×40 cm; 2 liters) packed with a mixture of acetone:water (10:0.5 v/v) and eluted with the same solvent mixture. 80 g. Fractions of the eluate were collected and fractions Nos. 16–24 collected. These active fractions were left to stand at a low temperature to precipitate neplanocin B in the form of white crystalline plates. 2.57 g. of crystalline neplanocin B were obtained (yield 32.8%).

EXAMPLE 3

Culturing was carried out as described in Example 1 to give about 200 liters of cultured mass which was filtered off and the cells washed with water. The filtrate and wash water were combined to give 140 liters (potency about 1.5 mcg/ml).

The solution was passed through a column of 20 liters of cation exchange resin "Amberlite" IR-120 (H+ type) to adsorb the material and washed with about 100 liters of water. Elution was carried out with 3.7 N aqueous ammonia solution and the primary eluate (30 liters) discarded. 90 liters of the following eluate were collected, adjusted to pH 8 by adding 6 N hydrochloric acid, then applied to a column of 4 liters of active carbon, washed with water and thereafter eluted with 90 liters of 70% aqueous methanol. The eluate thus obtained was concentrated to give 500 ml. of a concentrate which was freeze dried to give 31.2 g. of crude neplanocin F (purity about 0.5%).

EXAMPLE 4

The crude powder of neplanocin F obtained in Example 3 (31.2 g.) was applied to a column of silica gel (800 ml) packed with a mixture of n-butanol:28% aqueous ammonia solution:water (10:0.2:1 v/v/v) and eluted with the same solvent mixture. 150 ml. Fractions of the eluate were collected and fractions Nos. 5–10 were combined and concentrated in vacuo. The concentrate was applied to a silica gel column (240 ml) previously packed with a mixture of chloroform:methanol:acetic acid (10:2:0.2 v/v/v) and eluted with the same solvent mixture, 20 g. fraction being collected. Fractions Nos. 67–120 were combined and concentrated to give crude crystals of neplanocin F (108 mg; yield 51%).

EXAMPLE 5

The crude crystals of neplanocin F (108 mg) obtained in Example 4 were applied to a column of "Sephadex" G-15 (186 ml) packed with water and eluted with water. 10 g. Fractions were collected and fractions Nos. 22–27 were combined, concentrated to 5 ml. and left to stand in a refrigerator to precipitate neplanocin F in the form of white crystalline needles. The precipitate was filtered off and dried to give crystalline neplanocin F (87 mg) (yield 41%).
What is claimed is:
1. Neplanocins of the formula
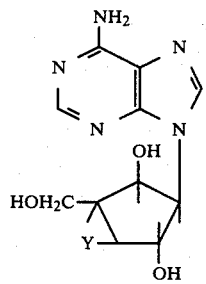
wherein Y is oxygen or a valence bond.
2. Neplanocin B of the formula
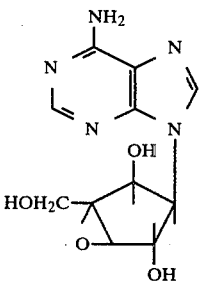
3. Neplanocin F of the formula
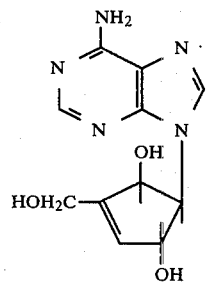
* * * * *